United States Patent
Tanaka et al.

(10) Patent No.: US 8,486,899 B2
(45) Date of Patent: *Jul. 16, 2013

(54) ANTIOXIDANT

(75) Inventors: Miyuki Tanaka, Zama (JP); Kouji Nomaguchi, Zama (JP); Tatsuya Ehara, Zama (JP)

(73) Assignee: Morinaga Milk Industry Co., Ltd., Minato-Ku, Tokyo (JP)

( * ) Notice: Subject to any disclaimer, the term of this patent is extended or adjusted under 35 U.S.C. 154(b) by 62 days.

This patent is subject to a terminal disclaimer.

(21) Appl. No.: 13/127,688

(22) PCT Filed: Nov. 18, 2009

(86) PCT No.: PCT/JP2009/069562
§ 371 (c)(1),
(2), (4) Date: May 4, 2011

(87) PCT Pub. No.: WO2010/058794
PCT Pub. Date: May 27, 2010

(65) Prior Publication Data
US 2011/0212910 A1    Sep. 1, 2011

(30) Foreign Application Priority Data

Nov. 19, 2008  (JP) ................................ 2008-295482

(51) Int. Cl.
*A61K 31/704* (2006.01)
(52) U.S. Cl.
USPC .......................................................... 514/26
(58) Field of Classification Search
USPC .......................................................... 514/26
See application file for complete search history.

(56) References Cited

U.S. PATENT DOCUMENTS

| | | | |
|---|---|---|---|
| 4,234,577 A | 11/1980 | Zilliken | |
| 5,565,207 A | 10/1996 | Kashibuchi et al. | |
| 6,087,345 A | 7/2000 | Ohta et al. | |
| 6,261,603 B1 | 7/2001 | McElwain | |
| 8,236,769 B2 * | 8/2012 | Tanaka et al. | 514/26 |
| 2003/0211177 A1 | 11/2003 | Pineda | |
| 2005/0048143 A1 | 3/2005 | McAnalley et al. | |
| 2008/0125379 A1 | 5/2008 | Tanaka et al. | |
| 2008/0255077 A1 | 10/2008 | Tanaka et al. | |
| 2009/0004307 A1 | 1/2009 | Tanaka et al. | |
| 2009/0054354 A1 | 2/2009 | Tanaka et al. | |
| 2009/0069254 A1 | 3/2009 | Tanaka et al. | |
| 2009/0075913 A1 | 3/2009 | Higuchi et al. | |
| 2009/0093450 A1 | 4/2009 | Tanaka et al. | |
| 2009/0131388 A1 | 5/2009 | Tanaka et al. | |
| 2009/0312275 A1 | 12/2009 | Tanaka et al. | |
| 2010/0035851 A1 | 2/2010 | Tanaka et al. | |
| 2010/0240632 A1 | 9/2010 | Higuchi et al. | |
| 2010/0286104 A1 | 11/2010 | Tanaka et al. | |

FOREIGN PATENT DOCUMENTS

| | | |
|---|---|---|
| JP | 05-051388 | 3/1993 |
| JP | 11-075770 | 3/1999 |
| JP | 2000-198726 | 7/2000 |
| JP | 2001-322934 | 11/2001 |
| JP | 2003-063926 | 3/2003 |
| JP | 2003-238344 | 8/2003 |
| JP | 2003-335625 | 11/2003 |
| JP | 2004-115375 | 4/2004 |
| JP | 2004-149729 | 5/2004 |
| JP | 2005-029490 | 2/2005 |
| JP | 2006-008719 | 1/2006 |
| JP | 2006-160668 | 6/2006 |
| JP | 2006-225310 | 8/2006 |
| JP | 2007-016077 | 1/2007 |
| WO | WO 2005/095436 | 10/2005 |
| WO | WO 2006/123464 | 11/2006 |
| WO | WO 2007/034851 | 3/2007 |
| WO | WO 2007/043302 | 4/2007 |

OTHER PUBLICATIONS

Definition of "prevention" from the Institute for International Medical Education [online], [Retrieved on Mar. 24, 2011]. Retrieved from the Internet <http://www.iime.org/glossary.htm>. Published Feb. 2002, p. 1, 2, 26, 27 and 39.*

Chander et al. Nephropathy in Zuker diabetic fat rat is associated with oxidative and nitrosative stress: Prevention by chronic therapy with a peroxynitrite scavenger Ebselen. J Am Soc Nephrol 15:2391-2403, Sep. 2004.*

Tinkel et al., Cardiovascular antioxidant therapy: A review of supplements, pharmacotherapies, and mechanisms. Cardiol Rev 20:77-83, Mar./Apr. 2012.*

Hu, et al. "Evaluation of Antioxidant Potential of *Aloe vera* (*Aloe barbadensis* Miller) Extracts," *Journal of Agricultural and Food Chemistry*, vol. 51, No. 26, pp. 7788-7791, 2003.

Singh, et al. "Chemomodulatory action of *Aloe vera* on the Profiles of Enzymes Associated with Carcinogen Metabolism and Antioxidant Status Regulation in Mice," *Phytomedicine*, vol. 7, No. 3, pp. 209-219, 2000.

Dinda, et al. Steroids and Terpenoid from *Mimosa pudica* Roots, Journal of the Indian Chemical Society, vol. 83, pp. 1044-1046, Oct. 2006.

International Search Report dated Feb. 9, 2010 issued to international application No. PCT/JP2009/069562.

Kunitomo, Masaru, "Oxidative Stress and Atherosclerosis," *Yakugaku Zasshi*, vol. 127, No. 12, pp. 1997-2014, 2007.

(Continued)

*Primary Examiner* — Wu-Cheng Winston Shen
*Assistant Examiner* — Yih-Horng Shiao
(74) *Attorney, Agent, or Firm* — Knobbe, Martens, Olson & Bear LLP

(57) ABSTRACT

To provide an antioxidant which is highly safe, inhibits oxidation of a biological component, in particular, a lipid, and is used as a drug, food or drink, a food additive, an external preparation for skin, or the like. The antioxidant contains 3-O-β-D-glucopyranosyl-4-methylergost-7-en-3-ol as an active ingredient.

7 Claims, No Drawings

OTHER PUBLICATIONS

Maeura, et al. "Dose-dependent Reduction of *N*-2-Fluorenylacetamide-induced Liver Cancer and Enhancement of Bladder Cancer in Rats by Butylated Hydroxytoluene," *Cancer Research*, vol. 44, pp. 1604-1610, Apr. 1984.

International Preliminary Report on Patentability dated Jun. 30, 2011 issued to international application No. PCT/JP2009/069562.

Botes, et al. "Phytochemical Contents and Antioxidant Capacities of Two *Aloe greatheadii* var. *davyana* Extracts," *Molecules*, vol. 13, No. 9, pp. 2169-2180, 2008.

Can, et al. "Effect of *Aloe vera* Leaf Gel and Pulp Extracts on the Liver in Type-II Diabetic Rat Models," *Biological & Pharmaceutical Bulletin*, vol. 27, No. 5, pp. 649-698, 2004.

Database: CAPLUS, Chopda, Patent No. IN 2006MU01831, "Herbal Compositions to Relieve Oxidative Stress," Accession No. 2007:441962, 2007, 5 pages.

Hu, et al. "Free Radical-scavenging Activity of *Aloe vera* (*Aloe barbadensis* Miller) Extracts by Supercritical Carbon Dioxide Extraction," *Food Chemistry*, vol. 91, No. 1, pp. 85-90, 2005.

Johnson, et al. "Plaque Rupture After Short Periods of Fat Feeding in the Apolipoprotein E-knockout Mouse, Model Characterization and Effects of Pravastatin Treatment," *Circulation*, vol. 111, No. 11, pp. 1422-1430, 2005.

Loots, et al. "*Aloe ferox* Leaf Gel Phytochemical Content, Antioxidant Capacity, and Possible Health Benefits," *J. Agric. Food Chem.*, vol. 55, No. 17, pp. 6891-6896, 2007.

Rajasekaran, et al. "Antioxidant Effect of *Aloe vera* Gel Extract in Streptozotocin-induced Diabetes in Rats," *Pharmacological Reports*, vol. 57, No. 1, pp. 90-96, 2005.

Rajasekaran, et al. "Modulatory Effects of *Aloe vera* Leaf Gel Extract on Oxidative Stress in Rats Treated with Streptozotocin," *Journal of Pharmacy and Pharmacology*, vol. 57, No. 2, pp. 241-246, 2005.

Tanaka, et al. "Identification of Five Phytosterols from *Aloe vera* Gel as Anti-diabetic Compounds," *Biol. Pharm. Bull.*, vol. 29, No. 7, pp. 1418-1422, 2006.

van Rensburg, et al. "A Comparative Study of the Effects of Cholesterol, Beta-sitosterol, Beta-sitosterol Glucoside, Dehydroepiandrosterone Sulphate and Melatonin on In Vitro Lipid Peroxidation," *Metabolic Brain Disease*, vol. 15, No. 4, pp. 257-265, 2000.

Yagi, et al. "Antioxidant, Free Radical Scavenging and Anti-inflammatory Effects of Aloesin Derivatives in *Aloe vera*," *Planta Medica*, vol. 68, No. 11, pp. 957-960, 2002.

Extended European Search Report dated Jul. 11, 2012, issued to the corresponding European patent application No. 09827575.3.

Patent Examination Report No. 2, dated Jul. 16, 2012, issued to the corresponding Australian patent application No. 2009318455.

Kim, et al. "Melatonin Reduces X-ray Irradiation-induced Oxidative Damages in Cultured Human Skin Fibroblasts," *Journal of Dermatological Science*, vol. 26, pp. 194-200, 2001.

Lomnitski, et al. "In Vitro and In Vivo Effects of β-Carotene on Rat Epidermal Lipoxygenases," *International Journal of Vitamin and Nutrition Research*, vol. 67, pp. 407-414, 1997.

Thiele, et al. In Vivo Exposure to Ozone Depletes Vitamins C and E and Induces Lipid Peroxidation in epidermal Layers of Murine Skin, *Free Radical Biology & Medicine*, VI. 23, No. 3, pp. 385-391, 1997.

\* cited by examiner

ANTIOXIDANT

CROSS-REFERENCE TO RELATED APPLICATIONS

This application is the U.S. National Phase under 35 U.S.C. §371 of International Application PCT/JP2009/069562, filed Nov. 18, 2009, which was published in a non-English language, which claims priority to JP Application No. 2008-295482, filed Nov. 19, 2008.

TECHNICAL FIELD

The present invention relates to an antioxidant which can be used as a drug, food or drink, a food additive, an external preparation for skin, or the like.

BACKGROUND ART

"Oxidative stress" is defined as a state where a living body has oxidative tendency as a result of an imbalance between production of reactive oxygen species (ROS) and antioxidative defense mechanisms in a living body. That is, excessive production of the ROS or a decrease in antioxidative ability leads to the oxidative stress.

The ROS oxidizes a lipid, in particular, a low-density lipoprotein (LDL) of a phopholipid to form a lipid peroxide and oxidized LDL, and oxidatively denatures and deactivates a protein to cause an oxidative damage of DNA. It is therefore said that the oxidative stress is involved in development of many diseases such as arteriosclerosis, cancer, various lifestyle-related diseases, Alzheimer's disease, and Parkinson's disease and promotes aging, through damages of cells and tissues and impairment of vital functions (for example, see Non Patent Document 1).

Further, the skin is in a state in which the ROS is easily produced by an irritation of an environmental factor such as an ultraviolet ray. The ROS in the skin causes, for example, destruction of a body tissue such as collagen to damage cells, resulting in skin symptoms such as wrinkles, a decrease in elasticity, an inflammation, and pigmentation. Also, the ROS is known to oxidize proteins and lipids in the scalp to cause hair loss (for example, Patent Documents 1 and 2).

Meanwhile, if the concentration of the lipid peroxide increases in blood, the lipid peroxide itself or an oxidative decomposition product thereof is known to act directly on nucleic acids and proteins to cause angiopathy, hepatic dysfunction, cataract, or the like. Moreover, the lipid peroxide causes injury of vascular endothelial cells, enhancement of platelet aggregation, formation of foam cells, or the like, and hence is considered to be a cause of arteriosclerosis.

For example, it is known that a primary lesion of arteriosclerosis is caused by an oxidized low-density lipoprotein (LDL), and that the easiest method of detecting oxidation of LDL is measurement of lipid peroxide (for example, Non Patent Document 2).

As antioxidants from natural products, vitamin E, vitamin C, a neutral fraction of an extract of a *Helichrysum* plant (for example, Patent Document 1), an extract of *Chimaphila umbellata* (for example, Patent Document 2), and the like are known.

In particular, known drugs or the like for inhibiting formation of a lipid peroxide in a living body include an agent containing sesamin and/or episesamin as an active ingredient (for example, Patent Document 3), an agent characterized by containing fructo-oligosaccharide (for example, Patent Document 4), an agent containing, as an active ingredient, an extract obtained by extraction from leaves of *Psidium guajava* L. (for example, Patent Document 5), an agent for inhibiting formation of a lipid peroxide characterized by containing an extract of a plant native to Mexico with a scientific name of *Gnaphalium semiamlexicaule* (for example, Patent Document 6), an agent containing astaxanthin and/or an ester thereof (for example, Patent Document 7), and an agent containing both an *Apocynum venetum* L. extract and a vitamin C compound (for example, Patent Document 8).

Further, Patent Document 9 discloses an agent for inhibiting formation of a lipid peroxide as an external preparation for skin containing a steroid glycoside and/or triterpenoid glycoside and a sphingoglycolipid.

Moreover, antioxidants such as 3,5-tert-butyl-4-hydroxytoluene (BHT) and 2,3-tert-butyl-hydroxyanisole (BHA) have been developed to inhibit oxidation of a lipid or the like. However, such antioxidants may be carcinogens (for example, Non Patent Document 3) and are difficult to use safely.

Under such circumstances, development of a novel antioxidative substance which can be used safely and has no side effects has been desired.

Note that, an agent for improving hyperglycemia, an agent for improving pancreatic function, an agent for improving insulin resistance, and an agent for inhibiting visceral fat accumulation, each of which contains 3-O-β-D-glucopyranosyl-4-methylergost-7-en-3-ol as an active ingredient, are known (Patent Documents 10, 11, 12, and 13, respectively).

PRIOR ART DOCUMENTS

Patent Document

[Patent Document 1] JP-A-2007-016077
[Patent Document 2] JP-A-2004-149729
[Patent Document 3] JP-A-5-51388
[Patent Document 4] JP-A-8-325157
[Patent Document 5] JP 11-75770
[Patent Document 6] JP-A-2000-198726
[Patent Document 7] JP-A-2006-8719
[Patent Document 8] JP-A-2006-160668
[Patent Document 9] JP-B-2886306
[Patent Document 10] WO2005/095436
[Patent Document 11] WO2006/123464
[Patent Document 12] WO2007/043302
[Patent Document 13] WO2007/034851

Non Patent Document

[Non Patent Document 1] YAKUGAKU ZASSHI, 127(12) 2007, 1997-2014
[Non Patent Document 2] "Oxidative Stress Navigator," Masahiko Kurabayashi, Ed., Medical Review Co., Ltd., 2005, 192-193
[Non Patent Document 3] Cancer Research, 44, 1984, 1604-1610

SUMMARY OF INVENTION

An object of the present invention is to provide an antioxidant which is highly safe, inhibits oxidation of a biological component, in particular, a lipid, and can be used as a drug, food or drink, a food additive, an external preparation for skin, or the like. In particular, an object of the present invention is to provide a drug, food or drink, or the like for inhibiting formation of a lipid peroxide, which effectively inhibits formation of a lipid peroxide in blood.

The first invention for solving the above-mentioned problem is an antioxidant containing a compound represented by the following chemical formula (1) as an active ingredient (hereinafter, referred to as "antioxidant of the present invention") and includes the following preferred embodiments (1) to (6):
(1) containing the compound represented by the chemical formula (1) at a concentration of at least 0.0001% by mass;
(2) being used for inhibiting oxidation of a lipid;
(3) being used for inhibiting formation of a lipid peroxide;
(4) being an external preparation for skin;
(5) consisting of food or drink containing the compound represented by the chemical formula (1); and
(6) containing an emulsifier.

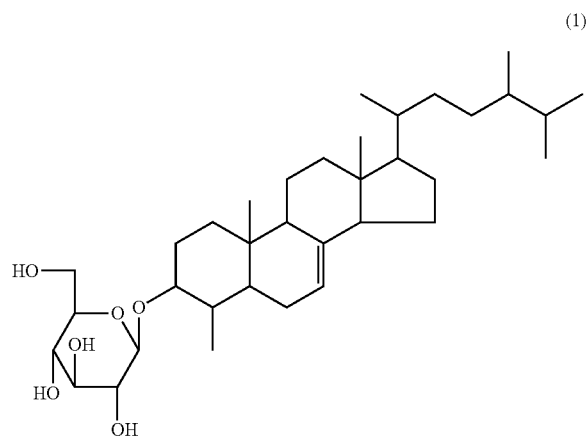

(1)

The second invention for solving the above-mentioned problem is a method of manufacturing an antioxidant, which includes blending the compound represented by the chemical formula (1) as an active ingredient.

The first invention includes an embodiment of a drug for inhibiting formation of a lipid peroxide, which contains the compound represented by the chemical formula (1) as an active ingredient. The embodiment includes the following preferred embodiment (7):
(7) containing the compound represented by the chemical formula (1) at a concentration of at least 0.0001% by mass.

The second invention includes an embodiment of a method of manufacturing a drug for inhibiting formation of a lipid peroxide, which includes mixing the compound represented by the chemical formula (1) as an active ingredient.

The first invention includes an embodiment of food or drink for inhibiting formation of a lipid peroxide, which contains the compound represented by the chemical formula (1) as an active ingredient. The embodiment includes the following preferred embodiments (8) to (11):
(8) containing the compound represented by the chemical formula (1) at a concentration of at least 0.0001% by mass;
(9) further containing an emulsifier;
(10) containing a fat and oil; and
(11) being a functional drink or food.

The second invention includes an embodiment of a method of manufacturing food or drink for inhibiting formation of a lipid peroxide, which includes mixing the compound represented by the chemical formula (1) as an active ingredient.

The first invention includes an embodiment of a food additive for inhibiting formation of a lipid peroxide, which contains the compound represented by the chemical formula (1) as an active ingredient. The embodiment includes the following preferred embodiments (12) and (13):
(12) further containing an emulsifier; and
(13) containing the compound represented by the chemical formula (1) at a concentration of at least 0.001% by mass.

The second invention includes an embodiment of a method of manufacturing a food additive for inhibiting formation of a lipid peroxide, which includes mixing the compound represented by the chemical formula (1) as an active ingredient. An embodiment of mixing an emulsifier is also preferred.

The third invention for solving the above-mentioned problem is use of the compound represented by the chemical formula (1) in the manufacture of an antioxidant.

Further, the third invention includes the following embodiment:
(14) use of a composition containing the compound represented by the chemical formula (1) at a concentration of at least 0.0001% by mass in the manufacture of an antioxidant.

The third invention includes an embodiment of use of the compound represented by the chemical formula (1) in the manufacture of a drug for inhibiting formation of a lipid peroxide.

Further, the embodiment includes the following embodiment:
(15) use of a composition containing the compound represented by the chemical formula (1) at a concentration of at least 0.0001% by mass in the manufacture of a drug for inhibiting formation of a lipid peroxide.

The third invention includes an embodiment of use of the compound represented by the chemical formula (1) in the manufacture of food or drink for inhibiting formation of a lipid peroxide.

Further, the embodiment includes the following embodiment:
(16) use of a composition containing the compound represented by the chemical formula (1) at a concentration of at least 0.0001% by mass in the manufacture of food or drink for inhibiting formation of a lipid peroxide.

The third invention also includes an embodiment of use of the compound represented by the chemical formula (I) in the manufacture of a food additive for inhibiting formation of a lipid peroxide.

Further, the embodiment includes the following embodiment:
(17) use of a composition containing the compound represented by the chemical formula (I) at a concentration of at least 0.001% by mass in the manufacture of a food additive for inhibiting formation of a lipid peroxide.

The fourth invention for solving the above-mentioned problem is a compound which is represented by the chemical formula (1) for use in antioxidation. Further, the compound is preferably for use in inhibiting oxidation of a lipid and is preferably for use in inhibiting formation of a lipid peroxide.

The fourth invention includes an embodiment of a composition containing the compound which is represented by the chemical formula (1) for use in antioxidation. The composition includes the following preferred embodiments:
(18) a composition containing the compound represented by the chemical formula (1) and an emulsifier; and
(19) a composition containing the compound represented by the chemical formula (1) at a concentration of at least 0.0001% by mass.

Further, the fifth invention for solving the above-mentioned problem is a method of treating or preventing a disease or symptom attributed to oxidation, the method including administering the compound represented by the chemical formula (1) to a subject who requires antioxidation.

Further, the fifth invention includes the following preferred embodiments (20):

(20) administering a composition containing the compound represented by the chemical formula (1) at a concentration of at least 0.0001% by mass.

Further, the sixth invention for solving the above-mentioned problem is a method of imparting an antioxidative activity to food or drink, the method including adding the compound represented by the chemical formula (1) to the food or drink so that the concentration of the compound in the food or drink is at least 0.0001% by mass.

The seventh invention for solving the above-mentioned problem is a method of enhancing an antioxidative activity of food or drink containing the compound represented by the following chemical formula (1), the method including adding the compound to the food or drink so that the concentration of the compound in the food or drink is at least 0.0001% by mass.

The antioxidant of the present invention may be used in various forms including a drug, food or drink, a food additive, and an external preparation for skin, and inhibits oxidation of a biological component, in particular, oxidation of a lipid.

The drug of the present invention can be administered safely and effectively inhibits oxidation of a biological component, in particular, formation of a lipid peroxide in blood. Further, the food or drink of the present invention can be ingested safely and effectively inhibits oxidation of a biological component, in particular, formation of a lipid peroxide in blood. In addition, the food additive of the present invention is suitable for manufacture of the above-mentioned food or drink or for prevention of oxidation of a component in food or drink. Moreover, the external preparation for skin of the present invention can be applied safely and effectively inhibits oxidation of a skin component, in particular, formation of a lipid peroxide in the skin.

Further, the active ingredient in the antioxidant of the present invention, 3-O-β-D-glucopyranosyl-4-methylergost-7-en-3-ol, can be manufactured by chemical synthesis, and according to the manufacture method of the invention of the present application, the antioxidant of the present invention can be easily manufactured. In addition, the active ingredient in the antioxidant of the present invention is known to be safe from the dietary experiences and can be easily manufactured from a plant of family Liliaceae which is easily available, for example, a plant such as *Aloe barbadensis* Miller. Therefore, according to the manufacture method of the invention of the present application, the antioxidant of the present invention can be easily manufactured.

DESCRIPTION OF EMBODIMENTS

Hereinafter, preferred embodiments of the present invention are described in detail. However, the present invention is not limited to the following preferred embodiments and any modification may be made within the scope of the present invention. Note that, in this description, all percentages are expressed as mass percentage unless otherwise specified.

The antioxidant of the present invention contains 3-O-β-D-glucopyranosyl-4-methylergost-7-en-3-ol as an active ingredient.

[Compound Serving as Active Ingredient of Present Invention]

The compound serving as an active ingredient in the antioxidant of the present invention is a compound having a structure represented by the following chemical formula (1), that is, 3-O-β-D-glucopyranosyl-4-methylergost-7-en-3-ol. The compound of the present invention has a structure obtained by dehydration condensation of the hydroxy group at position 3 of 4-methylergost-7-en-3-ol and the hydroxy group at position 1 of D-glucose.

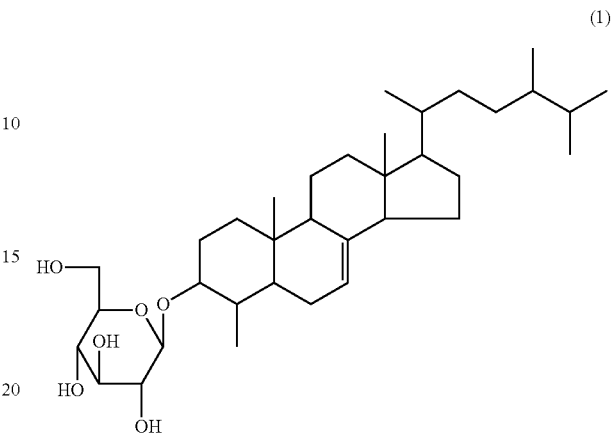

(1)

The compound of the present invention can be manufactured by, for example, synthesizing 4-methylergost-7-en-3-ol according to the supplement data described in PLOS BIOLOGY, vol. 2, p. e280 and performing condensation with D-glucose.

Further, the condensation of 4-methylergost-7-en-3-ol and D-glucose can be performed by, for example, using methods described in Jikken Kagaku Kouza 26, 4th edition, 1992, pp. 272, 297, and 342 in combination. Specifically, the condensation can be performed by completely acetylating D-glucose, converting the anomeric position into α-bromide, reacting 4-methylergost-7-en-3-ol with α-bromide in diethyl ether to β-glycosylate, and hydrolyzing the acetyl group in sodium methoxide/methanol.

Also, 4-methylergost-7-en-3-ol may be obtained by extraction and purification from plants.

In addition, it is known that 3-O-β-D-glucopyranosyl-4-methylergost-7-en-3-ol is contained in plants such as Liliaceae plants (JP-B-3883563). Therefore, the compound may be extracted from such plants by a method such as organic solvent extraction or hot water extraction.

The molecular weight and structure of the compound manufactured as above may be determined or confirmed by, for example, mass spectrometry (MS) and nuclear magnetic resonance spectrometry (NMR).

Further, 3-O-β-D-glucopyranosyl-4-methylergost-7-en-3-ol may be a pharmaceutically acceptable salt. The pharmaceutically acceptable salt includes both a metal salt (inorganic salt) and organic salt. Examples thereof include salts described in Remington's Pharmaceutical Sciences, 17th edition, 1985, p. 1418.

Specific examples of the salt include, but are not limited to: inorganic acid salts such as a hydrochloride, a sulfate, a phosphate, a diphosphate, a hydrobromide, and a sulfate; and organic acid salts such as a malate, a maleate, a fumarate, a tartrate, a succinate, a citrate, an acetate, a lactate, a methanesulfonate, a p-toluenesulfonate, a pamoate, a salicylate, and a stearate.

Meanwhile, each of those salts may be a salt of a metal such as sodium, potassium, calcium, magnesium, or aluminum, or a salt with an amino acid such as lysine. Moreover, there may also be used a solvate such as a hydrate of the above-mentioned compound or a pharmaceutically acceptable salt thereof.

[Antioxidant of Present Invention]

The antioxidant of the present invention contains 3-O-β-D-glucopyranosyl-4-methylergost-7-en-3-ol as an active ingredient.

The concentration of 3-O-β-D-glucopyranosyl-4-methylergost-7-en-3-ol in the antioxidant of the present invention may be appropriately selected depending on a target disease or a subject to be administered. The concentration is preferably at least 0.0001% by mass, more preferably at least 0.001% by mass, still more preferably at least 0.005% by mass, or particularly preferably at least 0.01% by mass. Further, the upper limit of the concentration of the compound in the drug of the present invention is not particularly limited, and for example, the concentration is 90% by mass or less, preferably 70% by mass or less, or more preferably 50% by mass or less.

The antioxidant of the present invention may be used in the form of a drug, food or drink, a food additive, an external preparation for skin, or the like.

(Drug of Present Invention)

The antioxidant of the present invention in the form of a drug (referred to as "drug of the present invention") may be administered orally or parenterally to a mammal including a human.

The drug of the present invention can be used for preventing and/or treating a disease or symptom attributed to oxidation of a biological component such as a lipid, in particular, formation of a lipid peroxide. Examples of such disease or symptom include arteriosclerosis, cerebral stroke, angina pectoris, myocardial infarction, hepatic dysfunction, hepatic cirrhosis, hepatitis, retinopathy, cataract, Alzheimer's disease, Parkinson's disease, allergic disease, cancer, skin roughness, aging, atopic dermatitis, and pigmentation such as blotches and freckles, wrinkles and a decrease in elasticity, alopecia, rheumatoid arthritis, Behcet's disease, and other tissue disorders, shoulder stiffness, and excessive sensitivity to cold. Of those, in particular, the drug of the present invention exhibits a remarkable effect on prevention and/or treatment of arteriosclerosis, angina pectoris, and myocardial infarction.

In addition, the drug of the present invention is useful for a person in need of prevention of disease events or reduction of a risk for onset of the events, that is, a person having a risk of an increase in lipid peroxide in a living body.

The dosage form of the drug of the present invention is not particularly limited and may be selected depending on therapeutic purposes or dose regimen. Specific examples thereof include a tablet, a pill, a powder, a liquid, a suspension, an emulsion, a granule, a capsule, a syrup, a suppository, an injection, an ointment, a patch, an ophthalmic solution, and a nasal drop.

The administration time of the drug of the present invention is not particularly limited and may be appropriately selected depending on a target disease. Meanwhile, the dose is preferably determined depending on a dosage form, dose regimen, age and sex of a patient, other conditions, degree of symptom, or the like.

The dose of the drug of the present invention is appropriately selected depending on a dose regimen, age or sex of a patient, degree of the symptom, other conditions, or the like. Usually, the dose is in the range of preferably 0.001 to 50 mg/kg/day, or more preferably 0.01 to 1 mg/kg/day in terms of the amount of the active ingredient.

Therefore, one of preferred embodiments of the drug of the present invention is a drug which is used such that the compound represented by the chemical formula (1) is administered in an amount of preferably 0.001 to 50 mg/kg/day, or more preferably 0.01 to 1 mg/kg/day.

The drug of the present invention may contain an additive which is generally used for drugs for inhibiting formation of a lipid peroxide. Examples of the additive include a filler, a binder, a disintegrant, a lubricant, a stabilizer, a flavoring agent, a diluent, a surfactant, and a solvent for injection. Further, the drug of the present invention may contain active ingredients corresponding to diseases or symptoms to be prevented or treated, for example, other ingredients each having an action of improving and/or preventing arteriosclerosis, cerebral stroke, hepatic dysfunction, or the like, as long as the antioxidative activity of 3-O-β-D-glucopyranosyl-4-methylergost-7-en-3-ol is not impaired.

The drug of the present invention can be manufactured by mixing, as an active ingredient, 3-O-β-D-glucopyranosyl-4-methylergost-7-en-3-ol in a carrier for drug. The drug of the present invention can be manufactured by, for example, formulating the above-mentioned compound together with the additive as described above.

Also, the drug of the present invention can be manufactured by formulating an extract, which is obtained by extracting a fraction containing the above-mentioned compound with an organic solvent or hot water from a known plant containing the above-mentioned compound or part thereof or a homogenate thereof and concentrating the fraction, together with the additive the described above.

The drug of the present invention can be manufactured by, for example, using an extract obtained by homogenizing mesophyll (clear gel) part of *Aloe barbadensis* Miller not containing the leaf skin to liquefy and performing extraction with an organic solvent or hot water.

In this case, examples of the organic solvent include alcohols such as methanol, ethanol, and butanol; esters such as methyl acetate, ethyl acetate, propyl acetate, and butyl acetate; ketones such as acetone and methyl isobutyl ketone; ethers such as diethyl ether and petroleum ether; hydrocarbons such as hexane, cyclohexane, toluene, and benzene; halogenated hydrocarbons such as carbon tetrachloride, dichloromethane and chloroform; heterocyclic compounds such as pyridine, glycols such as ethylene glycol; polyalcohols such as polyethylene glycol; nitrile solvents such as acetonitrile; and a mixed solution of those solvents. Further, those solvents may or may not contain water. Of those solvents, an ethyl acetate/butanol mixed solution (3:1) or a chloroform/methanol mixed solution (2:1) is preferred.

As an extraction method, a general extraction method used for extraction of plant components may also be used. In general, the method includes a method involving performing heat reflux for 1 part by mass of a fresh plant or a dried plant and 1 to 300 parts of an organic solvent with stirring or shaking at a temperature equal to or lower than the boiling point of the solvent or ultrasonic extraction for the plant at room temperature. If insoluble matters are separated from the resultant extract by an appropriate method such as filtration or centrifugation, a crude extract can be obtained. The crude extract can be purified by various kinds of chromatography such as normal-phase or reverse-phase silica gel chromatography. In the normal-phase silica gel chromatography, if a gradient of a chloroform/methanol mixed solution is used as an elution solvent, the active ingredient in the drug of the invention of the present application, 3-O-β-D-glucopyranosyl-4-methylergost-7-en-3-ol, is eluted at a ratio of chloroform:methanol of about 5:1.

The drug of the present invention may be used singly or together with an agent for preventing/treating such known disease as described above. If the drug is used together with the agent, the effect of preventing/treating the above-mentioned disease can be enhanced. The agent for preventing/treating the above-mentioned disease to be used together may be contained in the drug of the present invention as an active ingredient, or may be commercialized as a separate agent without mixing the agent in the drug of the present invention to provide a kit including the drug and agent to be used in combination.

The drug of the present invention exerts an excellent effect of inhibiting formation of a lipid peroxide because of the antioxidative action of 3-O-β-D-glucopyranosyl-4-methylergost-7-en-3-ol.

(Food or Drink of Present Invention)

In the case where the antioxidant of the present invention is used in the form of food or drink (referred to as "food or drink of the present invention"), the food or drink can be used for reducing the risk of a disease or symptom attributed to oxidation of a biological component such as a lipid, in particular, formation of a lipid peroxide or for preventing such disease or symptom.

The food or drink of the present invention contains 3-O-β-D-glucopyranosyl-4-methylergost-7-en-3-ol as an active ingredient.

In the present invention, the "food or drink" includes not only food or drink which is ingested by a human but also a feed which is ingested by animals other than a human.

The concentration of 3-O-β-D-glucopyranosyl-4-methylergost-7-en-3-ol in the food or drink of the present invention is appropriately set depending on the form of the food or drink. The concentration is preferably at least 0.0001% by mass, more preferably at least 0.001% by mass, still more preferably at least 0.005% by mass, or particularly preferably at least 0.01% by mass. The upper limit of the concentration of the compound in the food or drink of the present invention is not particularly limited, and for example, the concentration is 90% by mass or less, preferably 70% by mass or less, or more preferably 50% by mass or less.

Further, the concentration of the above-mentioned compound in the food or drink of the present invention may be set to an concentration suitable for ingestion in the range of 0.001 to 50 mg/kg/day, or more preferably 0.01 to 1 mg/kg/day depending on the form of the food or drink. Therefore, one of preferred embodiments of the food or drink of the present invention is food or drink which is used so that the above-mentioned compound may be ingested in an amount of preferably 0.001 to 50 mg/kg/day, or more preferably 0.01 to 1 mg/kg/day.

The food or drink of the present invention preferably further contains an emulsifier. The emulsifier is not particularly limited as long as it can be used in food. For example, emulsifiers which are approved as food additives in Japan, such as glycerin fatty acid ester, sucrose fatty acid ester, sorbitan fatty acid ester, propylene glycol fatty acid ester, and lecithins, are preferably used.

The food or drink further containing an emulsifier has a high ability to disperse the compound represented by the chemical formula (1) and can provide its effect very stably.

Further, if the compound represented by the chemical formula (1) may be processed into food or drink containing a fat and oil, or preferably food or drink containing a fat and oil as a major component, it is possible to provide food or drink having excellent storage stability because deterioration due to oxidation of a lipid is inhibited. The concentration of the above-mentioned compound is as mentioned above. Also, such food or drink is preferably emulsified. Examples of the food or drink containing a fat and oil include edible oil, dressing, mayonnaise, butter, margarine, and cream. The emulsified food is preferably contains an emulsifier. Preferred emulsifiers are as mentioned above.

The food or drink of the present invention is preferably a functional food or drink.

The "functional food or drink" means food which directly or indirectly indicates the effect of preventing a disease or the effect of reducing a risk of disease development. Examples thereof include foods which are now sold in Japan as foods for specified health use and health supplements.

Examples of the form of the food or drink of the present invention include drinks such as a soft drink, a carbonated drink, a nutritional drink, a fruit juice drink, and a lactic acid bacteria drink (including concentrated stock solutions of those drinks and powders for preparation of those drinks); ices such as an ice cream, an ice sherbet, and a shaved ice; noodles such as a buckwheat noodle, a wheat noodle, bean-starch vermicelli, a dumpling wrap, a su my wrap, a Chinese noodle, and an instant noodle; confectionery such as a hard candy, a chewing gum, a candy, a gum, chocolate, tablet confectionery, a snack, a biscuit, a jelly, a jam, a cream, and baked confectionery; processed marine and livestock products such as a boiled fish paste, ham, and sausage; dairy products such as processed milk, a milk drink, fermented milk, and butter; a daily dish and bakery; other foods or drinks such as an enteral nutrition food, a fluid diet, milk for infants, and a sport drink.

In particular, the functional food or drink is preferably in the form of a granular, tablet, or liquid supplement because a person who ingests the food can easily recognize the amount of an active ingredient to be ingested.

The food or drink of the present invention preferably has an indication of a purpose such as "for antioxidation," "for inhibiting oxidation of a lipid," or "for inhibiting formation of a lipid peroxide." That is, the food or drink of the present invention is preferably sold as, for example, food or drink for inhibiting formation of a lipid peroxide, which has the indication of the purpose "for inhibiting formation of a lipid peroxide" and contains 3-O-β-D-glucopyranosyl-4-methylergost-7-en-3-ol as an active ingredient.

The "indication" includes all indications which inform consumers about the above-mentioned purposes. That is, the "indication" includes all indications which may remind and evoke anyone of the above-mentioned purposes regardless of indication aims, indication contents, and targets/media to be indicated.

Further, the phrase "has an indication" means an indication action to give recognition of the indication in relation to the food or drink (product).

The indication action is preferably one which gives the above-mentioned purposes directly to consumers. Specific examples thereof include a write-down action of the above-mentioned purposes for a product according to the food or drink of the present invention or a package of the product, an advertisement for the product, and a write-down action of the above-mentioned purposes for a price list or a deal Document (including one supplied by an electromagnetic method).

Meanwhile, the content of the indication (indication content) is preferably one which is approved by the government or the like (for example, an indication which is approved based on various institutions specified by the government and has a form based on the approbation).

Examples thereof include indications on a health food, a functional food or drink, an enteral food, food for special dietary use, food with health claims, food for specified health use, food with nutrient function claims, a quasi drug, and the like. In particular, the indication includes an indication approved by Health, Labour and Welfare Ministry, e.g., an indication approved by the system of food for specified health use or one similar to the system. Examples of the latter include an indication as food for specified health use, an indication as a conditional food for specified health use, an indication showing a possibility of affecting the structure or function of the body, and an indication of a decrease in a disease risk. Specifically, as a typical indication, there are exemplified an indication as food for specified health use specified by the ordinance for health promotion action (the Ordinance No. 86 of Japan Health, Labour and Welfare Ministry, Apr. 30, 2003) (in particular, an indication of a health purpose), and one similar to the indication.

Needless to say, the tenors showing the above-mentioned purposes are not limited to tenors of "for antioxidation," "for inhibiting oxidation of a lipid," and "for inhibiting formation of a lipid peroxide," and a tenor including or an expression which shows an antioxidative action or effect, or an action or effect of inhibiting formation of a lipid peroxide, and a tenor including an expression which relates to an action or effect of preventing a disease or symptom attributed to an ROS or a lipid peroxide, or an action or effect of reducing a risk of onset of the disease or symptom are included in the scope of the present invention. Examples thereof include "(for) a person with a higher level of a lipid peroxide," "for a person with a higher level of lipid peroxide," "(for) a person having a problem in a lipid peroxide level," and "for a person having a problem in a lipid peroxide level."

Further, the food or drink of the present invention preferably includes not only an indication of the above-mentioned purposes but also an indication of the above-mentioned active ingredient and an indication showing the association between the purposes and active ingredient.

The food or drink of the present invention can be manufactured by mixing, as an active ingredient, 3-O-β-D-glucopyranosyl-4-methylergost-7-en-3-ol. The food or drink of the present invention can be manufactured by, for example, mixing the above-mentioned compound with food or drink raw material, and processing the mixture.

Also, the food or drink of the present invention can be manufactured by processing an extract, which is obtained by extraction with hot water or various solvents from a known plant or the like as a raw material which contains the above-mentioned compound, together with a food or drink raw material. A specific method of obtaining the extract is as mentioned in the section "Drug of present invention."

Further, in the case where the form of the food or drink of the present invention is a granular, tablet, or liquid supplement, 3-O-β-D-glucopyranosyl-4-methylergost-7-en-3-ol serving as an active ingredient is preferably formulated together with: for example, sugars such as lactulose, maltitol, and lactitol, and other sugars such as dextrin and starch; proteins such as gelatin, soybean protein, and corn protein; amino acids such as alanine, glutamine, and isoleucine; polysaccharides such as cellulose and gum arabic; and fats and oils such as soybean oil and medium-chain triglyceride.

Food Additive of Present Invention

In the case where the antioxidant of the present invention is used in the form of a food additive (referred to as "food additive of the present invention"), the food additive, which has been added to food or drink, can be used for reducing the risk of a disease or symptom attributed to oxidation of a biological component such as a lipid, in particular, formation of a lipid peroxide or for preventing such disease or symptom.

Further, the food additive of the present invention may be added to food or drink for inhibiting oxidation of a component in the food or drink, for example, oxidation of a lipid, before use. It is particularly suited that the food additive of the present invention be added to food or drink containing a fat and oil, or preferably food or drink containing a fat and oil as a major component. Examples of the food or drink containing a fat and oil are as listed in the section "Food or drink of present invention."

The food additive of the present invention contains 3-O-β-D-glucopyranosyl-4-methylergost-7-en-3-ol as an active ingredient.

The concentration of 3-O-β-D-glucopyranosyl-4-methylergost-7-en-3-ol in the food additive of the present invention is appropriately set. The concentration is preferably at least 0.001% by mass, more preferably at least 0.01% by mass, still more preferably at least 0.05% by mass, or particularly preferably at least 0.1% by mass. Further, the upper limit of the concentration of the compound in the food additive of the present invention is not particularly limited, and for example, the concentration is 90% by mass or less, preferably 70% by mass or less, or more preferably 50% by mass or less.

The food additive of the present invention preferably further contains an emulsifier. The emulsifier is not particularly limited as long as it can be used in food. For example, emulsifiers which are approved as food additives in Japan, such as glycerin fatty acid ester, sucrose fatty acid ester, sorbitan fatty acid ester, propylene glycol fatty acid ester, and lecithins, are preferably used.

When an emulsifier is added to the food additive of the present invention, the dispersibility of 3-O-β-D-glucopyranosyl-4-methylergost-7-en-3-ol serving as an active ingredient of the food additive of the present invention in a water-soluble food or drink is improved.

The form of the food additive of the present invention is not particularly limited and may be a form such as a powder, a granule, a tablet, or a liquid, which is generally used in a food additive.

In the case where the food additive of the present invention contains the emulsifier as described above, the food additive particularly preferably has a form of an emulsifier. When the additive has such form, the dispersibility of 3-O-β-D-glucopyranosyl-4-methylergost-7-en-3-ol in a water-soluble food or drink is further improved.

The food additive of the present invention may contain an additive which is generally used, such as a filler, in addition to 3-O-β-D-glucopyranosyl-4-methylergost-7-en-3-ol serving as an active ingredient and an emulsifier. Also, the food additive of the present invention may contain another known component which is generally used in a food additive.

The food additive of the present invention can be manufactured by mixing 3-O-β-D-glucopyranosyl-4-methylergost-7-en-3-ol as an active ingredient. The food additive of the present invention may be manufactured by, for example, formulating the above-mentioned active ingredient preferably together with the above-mentioned emulsifier, optionally together with the above-mentioned additive or another component.

Also, the food additive of the present invention can be manufactured by formulating an extract, which is obtained by extraction with hot water or various solvents from a known plant or the like as a raw material which contains the above-mentioned compound, preferably together with the above-mentioned emulsifier, optionally together with the above-mentioned additive or another component. A specific method of obtaining the extract is as mentioned in the section "Drug of present invention."

The food additive of the present invention may be used for manufacturing the above-mentioned food or drink of the present invention. The amount of the food additive added to food or drink may be appropriately adjusted based on the amount of 3-O-β-D-glucopyranosyl-4-methylergost-7-en-3-ol serving as an active ingredient in the above-mentioned food or drink of the present invention.

Further, the food additive of the present invention preferably has an indication of a purpose such as "for antioxidation," "for inhibiting oxidation of a lipid," or "for inhibiting formation of a lipid peroxide."

The "indication" and "indication action" are as mentioned in the section "Food or drink of present invention."

(External Preparation for Skin of Present Invention)

The antioxidant of the present invention in the form of an external preparation for skin (referred to as "external preparation for skin of the present invention") can be used for treating or improving, or preventing skin symptoms attributed to oxidation of a biological component such as a lipid, in particular, formation of a lipid peroxide.

For example, the preparation can be used for improving or preventing pigmentation such as blotches or freckles, and dermatitis such as atopic dermatitis or acne, or for improving or preventing wrinkles, a decrease in elasticity, alopecia, and the like.

The external preparation for skin includes all of drugs, quasi drugs, and cosmetics.

The external preparation for skin can be manufactured by mixing the compound represented by the chemical formula (1) in a base material which is generally known. The method of extracting the compound or the like is as mentioned in "Drug of present invention."

[Method of Imparting Antioxidative Activity of Present Invention]

The present invention includes a method of imparting, to food or drink, an antioxidative activity, preferably an activity to inhibit oxidation of a lipid, or more preferably an activity to inhibit formation of a lipid peroxide, the method including adding the compound represented by the chemical formula (1) to the food or drink so that the concentration of the compound in the food or drink is at least 0.0001% by mass, preferably at least 0.001% by mass, still more preferably at least 0.005% by mass, or particularly preferably at least 0.01% by mass. In this case with regard to the definition of the "food or drink," the definition of the food or drink in the section "Food or drink of present invention" above is applied.

The "adding the compound . . . " includes adding a compound obtained by purification or synthesis as well as adding an extract obtained by concentrating the above-mentioned compound by extraction with hot water or various solvents from a known plant or the like as a raw material which contains the above-mentioned compound. A specific method of obtaining the extract is as mentioned in the section "Drug of present invention."

[Method of Enhancing Antioxidative Activity of Present Invention]

Further, the present invention includes a method of enhancing an antioxidative activity of food or drink containing the compound represented by the chemical formula (1), preferably an activity to inhibit oxidation of a lipid, or more preferably an activity to inhibit formation of a lipid peroxide, the method including adding the compound represented by the chemical formula (1) to the food or drink so that the concentration of the compound in the food or drink is at least 0.0001% by mass, preferably at least 0.001% by mass, still more preferably at least 0.005% by mass, or particularly preferably at least 0.01% by mass. Also in this case, the definition of the "food or drink," the definition of the food or drink in the section "Food or drink of present invention" above is applied.

The food or drink containing the compound represented by the chemical formula (1) includes food or drink containing an extract of a plant of family Liliaceae. Examples thereof include food or drink containing a mesophyll of an *Aloe* plant. As described above, the "adding the compound . . . " includes adding a compound obtained by purification or synthesis as well as adding the above-mentioned extract.

[Evaluation of Action of Inhibiting Formation of Lipid Peroxide]

The actions of inhibiting formation of a lipid peroxide of various test samples including the antioxidant of the present invention can be evaluated by using, as an index, the amount of a thiobarbituric acid (TBA) reactive substance (TBARS), for example. Specifically, it may be defined that the larger the amount of the TBARS, the larger the amount of a lipid peroxide formed.

Examples of the TBARS include malondialdehyde (MDA) which reacts with TBA under high-temperature and acidic conditions and is a natural by-product of a lipid peroxidation. An MDA-TBA adduct can be detected by measurement of an absorbance at 530 to 540 nm to perform colorimetric measurement of MDA.

Also, the action of inhibiting formation of a lipid peroxide of a test sample can be evaluated using ApoE gene-deficient mice, which are often used as model animals which develop arteriosclerosis by hypercholesterolemia (hyper-LDL-cholesterolemia) (for example, see Reference Document 1: "Saibokogaku (Cell Engineering)," Extra Issue, "Medical Experiment Manual" series, Strategy for Study of Arteriosclerosis+Hyperlipidemia, Shujunsha Co., 1st edition, 1st impression, published on Apr. 1, 1996, pp. 441-443).

The model mice do not exhibit obesity and are known to develop hyper-LDL-cholesterolemia, arteriosclerosis, and cardiovascular diseases in this order. Further, in the model mice, the lipid peroxide level is higher than that of normal mice, and formation of atherosclerotic lesions (plagues) in the artery is observed with time. Therefore, the action of inhibiting formation of a lipid peroxide of a test sample can be evaluated by administering the test sample to the model mice and measuring a lipid peroxide in blood of the model mice.

In addition, it is generally known that a primary lesion of arteriosclerosis is caused by oxidized LDL. Therefore, it is also possible to evaluate the action of reducing a risk of arteriosclerosis through inhibiting formation of a lipid peroxide of the test sample by counting the number of atherosclerotic lesions (plaques) in the artery of each model mouse treated with the test sample.

Production Example 1

Production of 3-O-β-D-glucopyranosyl-4-methylergost-7-en-3-ol

3-O-β-D-glucopyranosyl-4-methylergost-7-en-3-ol was extracted and purified from *Aloe barbadensis* Miller as described below.

100 kg of mesophyll (clear gel part) of *Aloe barbadensis* Miller were liquefied using a homogenizer, and 100 L of an ethyl acetate/butanol mixed solution were (3:1) were added, followed by stirring.

The mixture was left to stand overnight and separated into the ethyl acetate/butanol mixed solution and the aqueous layer, followed by collection of the ethyl acetate/butanol mixed solution. The ethyl acetate/butanol mixed solution was concentrated under reduced pressure, to thereby obtain 13.5 g of an extract of the ethyl acetate/butanol mixed solution.

A solution obtained by dissolving 13 g of the extract in 1 ml of a chloroform/methanol mixed solution (1:1) was passed through a column filled with 400 g of silica gel 60 (manufactured by Merck & Co., Inc.) to adsorb to the column, and elution was performed using the chloroform/methanol mixed solution by a stepwise gradient method where the concentration of methanol was increased in a stepwise fashion (mixing ratios of chloroform:methanol=100:1, 25:1, 10:1, 5:1, and 1:1). Of those fractions, the fraction eluted with chloroform: methanol=5:1 was dissolved in 1 ml of the chloroform/methanol mixture (1:1), and the resultant was passed through a column filled with 180 g of COSMOSIL 140 (manufactured by Nacalai Tesque, Inc.) to adsorb to the column. Then, elution was successively performed with 600 ml of a 85% methanol solution, 600 ml of a 95% methanol solution, and 100 ml of 100% methanol. 3-O-β-D-glucopyranosyl-4-methylergost-7-en-3-ol was concentrated and separated in the fraction eluted with 95% methanol, and the solvent of the fraction was removed to obtain 3-O-β-D-glucopyranosyl-4-methylergost-7-en-3-ol. The structure of the compound was confirmed by MS and NMR.

EXAMPLES

Hereinafter, the present invention is described in more detail by way of examples. However, the present invention is not limited to the following examples.

Example 1

Model animals which develop arteriosclerosis, ApoE gene-deficient mice, were used to examine the action of inhibiting formation of a lipid peroxide of 3-O-β-D-glucopyranosyl-4-methylergost-7-en-3-ol.

(1) Sample Preparation

3-O-β-D-glucopyranosyl-4-methylergost-7-en-3-ol manufactured in Production Example 1 above was used as a test sample, and Mevalotin (DAIICHI SANKYO COMPANY, LIMITED), which is an HMG-CoA reductase inhibitor, was used as a control sample.

Those samples were separately dissolved in physiological saline so that the concentration of each compound was 30 μg/ml and were used for a test. Note that physiological saline was used as a negative sample.

(2) Test Method

Six-week-old male ApoE gene-deficient mice (purchased from Japan SLC, Inc.) were preliminarily fed with a high-cholesterol diet (manufactured by Research Diets, Inc.) for 2 weeks and divided into groups each of 15 mice.

To mice of each group, the solution including the test sample, control sample, or negative sample was separately administered orally once a day for 3 consecutive days using medical probes in an amount of 1 ml per 25 g of mouse body weight. At an early period after the start of administration (14 days after the start of administration), blood was collected from the tail vein of each mouse, and serum was separated. Then, the amount of TBARS was measured using OxiSelect TBARS Assay Kit (manufactured by MDA Quantitation). Meanwhile, as a control, blood was collected from each normal mouse in the same manner as above.

(3) Test Results

Test results of this example are shown in Table 1. Table 1 shows the amount of a lipid peroxide in blood (MDA concentration in serum) in the case where a sample was administered to each mouse in an amount of 30 μg per day.

In the case of the mice treated with the negative sample, the lipid peroxide in blood was found to tend to increase compared with the normal mice. However, in the case of the model mice successively treated with the test sample, the effect of inhibiting formation of a lipid peroxide in blood was clearly confirmed (there is a significant difference, the symbol "*" in the table). The results show that administration of 3-O-β-D-glucopyranosyl-4-methylergost-7-en-3-ol to the ApoE gene-deficient mice leads to a decrease in the concentration of a lipid peroxide in blood to a level almost equal to that of the normal mice and is effective for preventing or treating arteriosclerosis.

On the other hand, in the case of the mice treated with the control sample (Mevalotin), a significant decrease in amount of a lipid peroxide in blood was not observed compared with the negative sample.

Note that side effects were not observed during administration of the test samples, and there was no abnormality in pathological findings after administration.

The above-mentioned results indicate that 3-O-β-D-glucopyranosyl-4-methylergost-7-en-3-ol has the effect of inhibiting formation of a lipid peroxide and is effective for preventing or treating arteriosclerosis.

TABLE 1

| Mouse/sample | | Amount of lipid peroxide in blood (MDA concentration (μM)) | p value |
|---|---|---|---|
| | Normal mouse | 0.5 ± 0.19 | — |
| ApoE gene-deficient mice | Test sample | 0.51 ± 0.22 | 0.0004* |
| | Control sample | 0.93 ± 0.05 | 0.11 |
| | Negative sample | 0.99 ± 0.06 | — |

Example 2

In Example 2, 3-O-β-D-glucopyranosyl-4-methylergost-7-en-3-ol was evaluated on the effect of reducing a risk of arteriosclerosis through the effect of inhibiting a lipid peroxide by counting the number of atherosclerotic lesions (plaques) in the artery using known arteriosclerosis model animals, ApoE gene-deficient mice.

(1) Sample Preparation

A test sample, a control sample, and a negative sample were prepared in the same way as in Example 1 above and were each used for a test.

(2) Test Method

Six-week-old male ApoE gene-deficient mice (purchased from Japan SLC, Inc.) were preliminarily fed with a high-cholesterol diet (manufactured by Research Diets, Inc.) for 2 weeks and divided into groups each of 15 mice.

Each of the sample solutions including the test sample, control sample, and negative sample was separately administered orally once a day for 39 consecutive days using medical probes in an amount of 1 ml per 25 g of mouse body weight. Forty days after the start of administration, the thoracic aorta part was fixed with formalin and stained with Oil red, and the number of plaques was counted.

(3) Test Results

The test results of this example are shown in Tale 2. Table 2 shows the numbers of atherosclerotic lesions (plaques) in the arteries of the model mice treated with the sample solutions.

The results revealed that the number of the plaques of the model mice treated with the negative sample was found to be 12.2, while the number of the plaques of the model mice treated with the test sample was found to decrease by half to 5.8, and the test sample had an effect of inhibiting plaque formation on the arterial endothelium (there is a significant difference, the symbol "*" in the table).

On the other hand, in the case of the mice treated with the control sample (Mevalotin), there was no significant difference although plaque formation was found to decrease compared with the negative sample.

Note that during and after administration, no side effects were observed in terms of the body weights and pathological findings of the mice.

The results clarified that 3-O-β-D-glucopyranosyl-4-methylergost-7-en-3-ol had an effect of inhibiting plaque formation in the vein and reduced a risk of arteriosclerosis through the effect of inhibiting a lipid peroxide.

TABLE 2

| Mouse/sample | | Number of plaques formed in thoracic aorta | p value |
|---|---|---|---|
| ApoE gene-deficient mouse | Test sample | 5.8 ± 1.6 | 0.007* |
| | Control sample | 10.6 ± 3.2 | 0.25 |
| | Negative sample | 12.2 ± 3.0 | — |

INDUSTRIAL APPLICABILITY

The antioxidant of the present invention can be administered safely and inhibits oxidation of a biological component, in particular, effectively inhibits formation of a lipid peroxide in blood. Therefore, the antioxidant is effective for treating and/or preventing diseases and symptoms such as arteriosclerosis, cerebral stroke, angina pectoris, myocardial infarction, hepatic dysfunction, hepatic cirrhosis, hepatitis, retinopathy, cataract, Alzheimer's disease, Parkinson's disease, allergic disease, cancer, skin roughness, and aging. Of those, the antioxidant of the present invention has a remarkable effect of treating and/or preventing arteriosclerosis, angina pectoris, and myocardial infarction. Accordingly, the drug of the present invention is useful for treating and preventing the above-mentioned diseases and symptoms. Further, the food or drink of the present invention is useful when ingested for preventing the above-mentioned diseases and symptoms and for reducing a risk of onset thereof because the food or drink can be ingested safely and effectively inhibits formation of a lipid peroxide in a living body, in particular, in blood. In addition, the food additive of the present invention is useful for manufacturing such food or drink and inhibiting oxidation of a component in food or drink. Moreover, the external preparation for skin of the present invention is useful for treating or improving or preventing pigmentation such as blotches or freckles, dermatitis such as atopic dermatitis or acne, or for improving or preventing wrinkles, a decrease in elasticity, alopecia, and the like.

What is claimed is:

1. A method of treating one or more disease or symptom of skin selected from the group consisting of skin roughness, skin aging, dermatitis, pigmentation, wrinkles, a decrease in skin elasticity and alopecia, comprising administering a compound represented by the following chemical formula (1) to a subject in need of treatment

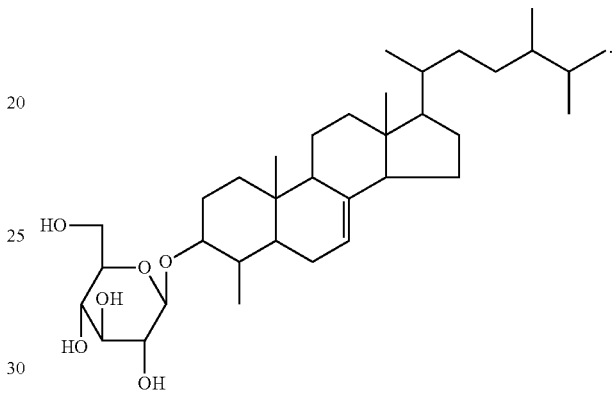

(1)

2. The method according to claim 1, comprising administering a composition containing the compound represented by the chemical formula (I) at a concentration of at least 0.0001% by mass.

3. The method according to claim 2, wherein the composition is a drug.

4. The method according to claim 2, wherein the composition is an external preparation for skin.

5. The method according to claim 2, wherein the composition is food or drink.

6. The method according to claim 5, wherein the food or drink contains an emulsifier.

7. The method according to claim 2, wherein the composition is a food additive, and containing at least 0.001% by mass of the compound.

* * * * *